United States Patent [19]
Chen et al.

[11] Patent Number: 4,827,068
[45] Date of Patent: May 2, 1989

[54] AROMATIZATION WITH CATALYST COMPRISING NOBLE-METAL CONTAINING TITANOSILICATE HAVING THE STRUCTURE OF ZEOLITE BETA

[75] Inventors: Nai Y. Chen, Titusville, N.J.; Sharon B. McCullen, Newtown, Pa.

[73] Assignee: Mobil Oil Corporation, New York, N.Y.

[21] Appl. No.: 138,974

[22] Filed: Dec. 29, 1987

[51] Int. Cl.$^4$ .................... C07C 11/20; C07C 2/52
[52] U.S. Cl. .................... 585/408; 585/417; 585/419
[58] Field of Search .................... 585/408, 417, 419

[56] References Cited

U.S. PATENT DOCUMENTS 4,645,864 2/1987 Chang et al. .................... 585/408
4,711,970 12/1987 Chang et al. .................... 585/419

Primary Examiner—Curtis R. Davis
Attorney, Agent, or Firm—Alexander J. McKillop; Charles J. Speciale; Robert B. Furr, Jr.

[57] ABSTRACT

Aromatization of non-aromatics is carried out by contacting with a titanosilicate having the structure of zeolite beta which contains noble metal.

12 Claims, No Drawings ly, catalysts of the present invention are par-
AROMATIZATION WITH CATALYST COMPRISING NOBLE-METAL CONTAINING TITANOSILICATE HAVING THE STRUCTURE OF ZEOLITE BETA The present invention relates to low acidity, noble metal-containing titanosilicate materials having the structure of zeolite beta, and their use as noble metal supports. This invention further relates to the use of these materials as catalysts in hydrocarbon processing, e.g., in aromatization reactions, including paraffin dehydrocyclization and naptha reforming.

Titanosilicates having the structure of zeolites are known in the art. U.S. Pat. No. 3,329,481 to Young teaches "crystalline titano-silicate zeolites" which are prepared by reacting peroxo alkali metal titanates with alkaline silicate solutions. U.S. Pat. No. 4,329,328 to McAnespie et al teaches a method of preparing titanosilicate material by mixing titanate solution with a source of silica. U.S. Pat. No. 4,410,501 to Taramasso et al discloses "titanium silicalite" designated TS-1 and its use in a wide variety of organic conversion reactions including isomerization of n-paraffins and naphthenes, reforming, and polymerization of compounds containing olefin bonds. The material is prepared from a reaction mixture containing sources of silicon oxide, titanium oxide, alkaline oxide, nitrogenated organic base and water. The titanium oxide source may include hydrolyzable $TiX_4$, where X is selected from the group consisting of F, Cl, Br and I. U.S. Pat. Nos. 4,519,998 and 4,623,526 relate to a process for preparing crystalline titanoborosilicate by reacting titanium-containing compound and an alkali tetrahydroborate, sodium silicate, and alkylammonium cation. These two references also teach exchanging noble metals with the titanoborosilicate and the use of titanoborosilicates in hydrocarbon conversion processes, including aromatization. Hydrogen forms of titanoborosilicate are taught as being prepared by calcining and ammonium-exchanging with ammonium chloride, ammonium nitrate ammonium acetate. U.S. Pat. No. 4,576,805 to Chang et al discloses a method for treating porous crystalline silicates, e.g., zeolite beta, by adding framework metals by contacting said silicates with volatile metal compounds, e.g., $TiCl_4$. All of the above references are incorporated herein by reference. U.S. application Ser. No. 138,972, filed Dec. 29, 1987; and U.S. Ser. No. 138,973, filed Dec. 29, 1987, filed contemporaneously with the present application relate to titanosilicates of low acidity and high ion exchange capacity which are prepared with aqueous alkaline solution treatment and noble metal-containing titanosilicates having the structure of zeolite beta.

The present invention relates to a noble metal-containing porous crystalline titanosilicate having the structure of zeolite beta.

Generally, catalysts of the present invention are particularly useful in any process or combination of processes which employ metal catalyst components such as platinum or palladium, as well as other noble metals. Examples of such processes include hydrogenation, dehydrogenation, dehydrocyclization, isomerization, hydrocracking, dewaxing, reforming, conversion of alkyl aromatics, oxidation, etc. The catalysts of the present invention are believed to be particularly useful in catalytic dehydrocyclization and aromatization of aliphatic feeds.

The present invention is of particular utility in that it can be used to prepare porous crystalline titanosilicates of relatively low acid activity. The low acidity characteristics are suited to use in hydrocarbon conversion reactions such as isomerization of paraffins, aromatization of aliphatics and oligomerization of olefins. Such reactions are optimized when a hydrogenation/dehydrogenation component such as noble metal is associated with the porous crystalline silicate. Highly siliceous porous crystalline silicates such as highly siliceous aluminosilicate zeolites exhibit the low acidity desired for such catalysts.

The titanosilicate employed can be any porous crystalline silicate material having the structure of zeolite beta wherein titanium is present in the framework. Titanosilicates prepared by inserting titanium into an existing framework of a porous crystalline silicate zeolite beta, e.g., by contact with volatile titanium compounds e.g., $TiX_4$ where X is selected from the group consisting of F, Cl, Br, and I, preferably Cl, as described in U.S. Pat. No. 4,576,805 or by contact with a liquid phase source of titanium, e.g., $(NH_4)_2TiF_6$(aq.) or $TiF_4$(aq.), are well-suited for use in the present invention.

The noble metal-containing catalysts of the present invention comprise a titanosilicate, having the structure of zeolite beta, a noble metal and, optionally, a binder.

For the purpose of this invention, the term "zeolite" is meant to represent the class of porotectosilicates, i.e., porous crystalline silicates that usually contain silicon and oxygen atoms as the major components. Other components may be present in minor amounts, usually less than 14 mole % and preferably less than 4 mole %. These components include aluminum, boron, gallium, iron, phosphorus and the like with aluminum being preferred. The minor components may be present separately or in mixtures. Titanosilicate zeolites contain titanium in the porous crystalline silicate framework and can include one or more of the above-named minor components in the framework as well, preferably aluminum and/or boron.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other forms within the channels. Although zeolites with a silica to alumina mole ratio of at least 12 are useful, it is preferred in some instances to use zeolites having much higher silica to alumina mole ratios. Thus zeolites useful in the present invention can have silica to alumina molar ratios of at least about 20, 25, 70, or in some instances at least 100 or even at least 150.

Zeolite beta is described in U.S. Pat. No. 3,308,069, the contents of which are incorporated herein by reference.

As is the case of many catalysts, it may be desired to incorporate the titanosilicate with another material resistant to the temperatures and other conditions employed in organic conversion processes. Such materials include active and inactive materials as well as inorganic materials such as clays, silica and/or metal oxides. Inactive materials suitably serve as diluents to control the amount of conversion in a given process so that products can be obtained economically without employing other means for controlling rate of reaction. Binders useful for compositing with the useful zeolite herein also include inorganic oxides, notably alumina, which is particularly preferred.

In addition to the foregoing material, the zeolite catalyst can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The relative proportions of finely divided crystalline zeolite and inorganic oxide matrix may vary widely with the zeolite content ranging from about 1 to about 90 percent by weight, and more usually in the range of about 10 to about 50 percent by weight of the composite.

The titanosilicate, having the structure of zeolite beta, is contacted with a source of noble metal to prepare the noble metal-containing titanosilicate of the present invention. Preferably, such contacting occurs with a solution comprising ionizable compound of a noble metal, e.g., platinium or palladium, for a sufficient period of time to effect deposition on the crystalline structure of the zeolite of a noble metal-containing ion derived from such a solution, drying the resulting product and optionally subjecting the same to an activating treatment.

The noble metals which can be incorporated in the present catalyst composition include those having atomic numbers 44 to 47 and 76 to 79 inclusive, namely platinum, palladium, ruthenium, osmium, iridium, rhodium, silver and gold. Of this group, platinum and palladium are accorded preference. Each of the noble metals may occur in a variety of compounds for example, compounds containing the platinum ammine complex such as $Pt(NH_3)_4(NO_3)_2$. The compounds of the useful noble metals can be ionizable noble metal compounds in which the metal is in the cationic state, i.e. in the form of a cation or cation complex, since with such compounds exchange of the original metal ion contained in the metal aluminosilicate crystalline zeolite with the platinum metal-containing cation is readily achieved.

A wide variety of metallic compounds can be employed with facility as a source of noble metal cations and include both inorganic and organic salts of the noble metals. Representative of the salts which can be employed are chlorides, bromides, iodides, carbonates, bicarbonates, sulfates, sulfites, sulfides, chlorates, perchlorates, thionates, thiocyanates, dithiocarbamates, peroxysulfates, acetates, benzoates, citrates, fluorides, nitrates, nitrites, formates, propionates, butyrates, valerates, lactates, malonates, oxalates, palmitates, hydroxides, tartarates and the like. The only limitation is that the salt be sufficiently soluble in the fluid medium to give the necessary ion transfer.

It is contemplated that water will ordinarily be the solvent in the noble metal-containing solutions used. However, it will be understood that other solvents, although generally less preferred, may also be used. Thus, in addition to aqueous solutions, alcoholic solutions, etc., of the noble metal-containing compounds may be employed in the present process. The compounds of the noble metals undergo ionization in the particular solvent used. The concentration of the noble metal compound in the solution employed may vary widely depending on the amount of noble metal desired in the final catalyst composition and on the conditions under which contact between the crystalline zeolite and such solution is effected. Other conditions being equal, a shorter time of contact between the crystalline zeolite and noble metal-containing solution may be used with the more concentrated solutions, while a longer period of contact is required with the more dilute solutions.

The solutions of noble metal compound may be contacted with the porous crystalline titanosilicate in the form of either a fine powder, a compressed pellet or an extruded pellet. When in the form of a pellet, the crystalline titanosilicate may be combined with a suitable binder such as clay. The crystalline titanosilicate is initially free of noble metal having rigid three dimensional networks characterized by uniform interstitial dimensions sufficiently large to permit introduction by ion exchange of a noble metal-containing ion. The metal originally contained in the titanosilicate will generally be an alkali or alkaline earth metal, e.g., sodium or calcium, although these may be replaced at least in part by other ions which do not ordinarily affect the crystalline structure such as for example silver, lithium, potassium, magnesium, cobalt and also ammonium ions.

The volume of solution containing noble metal compound may be just sufficient to be adsorbed by the crystalline titanosilicate. Generally, however, an excess of solution is employed and such excess is removed from contact with the crystalline titanosilicate after a suitable period of contact and prior to drying. The time of contact between the solution of noble metal compound and crystalline material is such as to effect deposition on the crystalline structure of the noble metal-containing ion derived from such solution. It will be appreciated that such period of contact may vary widely depending on the temperature of the solution, the nature of crystalline material used, the particular noble metal compound employed, and the concentration of noble metal desired in the final catalyst. Thus, the time of contact may extend from a very brief period of the order of minutes for small particles to long periods of the order of days for large pellets. Generally, the time of contact will, depending on the various aforementioned factors, be within the range of 5 minutes to 10 days. The temperature of the solution will ordinarily be room temperature, but may be an elevated temperature below the boiling point of the solution.

After the contact period, the crystalline titanosilicate is removed from the noble metal compound solution. Excess noble metal compound and foreign salt, if employed, are removed, suitably by washing with water. The resulting material is then dried, generally in air, to remove substantially all of the water therefrom.

The noble metal catalyst of this invention contains noble metal deposited on the porous crystalline titanosilicate. The concentration of noble metal in the finished catalyst may vary depending on the use for which such catalyst is intended. The content of noble metal in the finished catalyst is generally within the approximate range of 0.001 to 5 percent by weight, preferably between about 0.05 and 2 weight percent, say about 0.6 weight percent.

The aromatization conditions suitable for use in accordance with the present invention may include, e.g., a temperature of from about 200° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

The feedstock to be aromatized may comprise, e.g. $C_2$–$C_{12}$ non-aromatic hydrocarbons, $C_1$–$C_5$ alcohols, $C_2$–$C_6$ ethers and/or other non-aromatic compounds capable of producing aromatic compounds. Examples of $C_2$–$C_{12}$ non-aromatic hydrocarbons include ethylene, propylene and/or propane. When these three hydrocarbons are present in admixture, the feedstock to be aromatized may comprise, e.g., from about 1 to about 30 weight percent of ethylene, from about 1 ato about 30 weight percent of propylene and from about 1 to about 30 weight percent of propane. This feedstock may be, e.g., a refinery off gas. An alcohol which may be aromatized is methanol. Dimethylether is an example of an ether which may be aromatized is dimethylether.

The invention can be further described by the following Examples.

EXAMPLE 1

A sample of zeolite beta containing framework boron containing 0.66 wt% B, 0.67 wt% $Al_2O_3$, 98.67 wt%. $SiO_2$, having a $SiO_2/Al_2O_3$ molar ratio of 250:1 and $SiO_2/Al_2O_3+B_2O_3$ molar ratio of 44:1, was treated with $TiCl_4$ vapor in $N_2$ for 4 hours at 450° C. and then calcined in air at 538° C. for 2 hours.

Elemental analysis before and after $TiCl_4$ treatment is set out in Table 1 and shows a decrease in milliequivalents/g ash of boron and alumina, 0.51, which is roughly equivalent to the milliequivalents/g ash of Ti, 0.59, gained.

The resulting product was then contacted with an excess solution of water and $Pt(NH_3)_4(NO_3)_2$ solution added dropwise to deposit 0.6 wt% Pt on the titanosilicate, 0.012 g of $Pt(NH_3)_4(NO_3)_2$ per g of titanosilicate. The product was filtered, washed, dried and then air calcined at 350° C. for 2 hours.

EXAMPLE 2

A sample of zeolite beta containing 0.66 wt.% B, 0.67 wt.% $Al_2O_3$, 98.67 wt.% $SiO_2/Al_2O_3$ molar ratio of 250:1 and $SiO_2/Al_2O_3+B_2O_3$ molar ratio of 44:1 was contacted with an excess solution of water. A $Pt(NH_3)_4(NO_3)_2$ solution was added dropwise to obtain 0.012 g of $Pt(NH_3)_4(NO_3)_2$ per gram of zeolite beta. The product was filtered, washed, dried and then air calcined at 350 C. for 2 hours.

EXAMPLE 3

The platinum-containing catalysts of Examples 1 and 2 were used to process a model feed containing 25 wt% methylcyclopentane (MCP) and 75 wt% n-heptane at 250 psi, 4 LHSV, $H_2:HC=6:1$, 875 and 900° F. The reaction products and yields are shown in Table 1 below.

A comparison of the products and yields of the catalysts show that the titanosilicate is more selective for dehydrocyclization of n-heptane to $C_{7+}$ aromatics (toluene, xylenes, trimethylbenzenes) which are known to increase gasoline octane.

TABLE 1

Dehydrocyclization of n-Heptane with Catalysts of Examples 1 and 2

|  | Example 1 | | Example 2 | |
| --- | --- | --- | --- | --- |
| Temperature, °F. | 875 | 898 | 871 | 901 |
| Wt % from MCP | | | | |
| MCP | .050 | 0.23 | 0.45 | 0.25 |
| benzene | 15.7 | 15.6 | 4.3 | 6.3 |
| $CyC_6$ | 0.09 | 0.06 | 0.0 | 0.0 |
| $C_6-$ | 8.7 | 9.1 | 20.2 | 18.4 |
| Wt % from n-$C_7$ | | | | |
| n-$C_7$ | 0.02 | 0.0 | 0.0 | 0.0 |
| i-$C_7$ | 0.09 | 0.07 | 0.0 | 0.0 |
| $C_{7+}$ aromatics | 14.9 | 17.3 | 4.5 | 8.2 |
| $C_{7+}$ nap. | 0.5 | 0.5 | 0.5 | 0.5 |
| $C_6-$ | 59.5 | 57.1 | 70.0 | 66.3 |

We claim:

1. A process for producing aromatic hydrocarbons, said process comprising contacting a feedstock comprising one or more non-aromatic compounds with a titanosilicate having the structure of zeolite beta in which a noble metal has been incorporated into said titanosilicate by ion exchange, wherein said contacting takes place under aromatization conditions including a temperature of from about 200° to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

2. The process of claim 1 wherein said non-aromatic compounds are selected from the group consisting of $C_2-C_{12}$ non-aromatic hydrocarbons, $C_1-C_5$ alcohols, and $C_2-C_6$ ethers.

3. The process of claim 1 wherein said non-aromatic compounds are selected from the group consisting of $C_2-C_{12}$ alkanes and $C_2-C_{12}$ alkenes.

4. The process of claim 1 wherein said titanosilicate contains about 0.05 to about 2 weight percent platinum.

5. The process of claim 1 wherein said noble metal-containing titanosilicate is ion exchanged with ions selected from the group consisting of alkali metal and alkaline earth metal prior to said contacting.

6. The process of claim 1 wherein said noble metal is platinum.

7. A process for producing aromatic hydrocarbons, said process comprising contacting a feedstock comprising one or more non-aromatic compounds with a titanosilicate having the structure of zeolite beta in which a noble metal has been incorporated into said titanosilicate by impregnation, wherein said contacting takes place under aromatization conditions including a temperature of from about 200° to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

8. The process of claim 7 wherein said non-aromatic compounds are selected from the group consisting of $C_2-C_{12}$ non-aromatic hydrocarbons, $C_1-C_5$ alcohols, and $C_2-C_6$ ethers.

9. The process of claim 7 wherein said non-aromatic compounds are selected from the group consisting of $C_2-C_{12}$ alkanes and $C_2-C_{12}$ alkenes.

10. The process of claim 7 wherein said titanosilicate contains about 0.05 to about 2 weight percent platinum.

11. The process of claim 7 wherein said noble metal-containing titanosilicate is ion exchanged with ions selected from the group consisting of alkali metal and alkaline earth metal prior to said contacting.

12. The process of claim 7 wherein said noble metal is platinum.

* * * * *